(12) United States Patent
Kleiven et al.

(10) Patent No.: US 12,350,485 B2
(45) Date of Patent: Jul. 8, 2025

(54) TREATMENT DEVICE

(71) Applicants: Svein Kleiven, Stockholm (SE); Xiaogai Li, Solna (SE); Teng Wang, Huddinge (SE)

(72) Inventors: Svein Kleiven, Stockholm (SE); Xiaogai Li, Solna (SE); Teng Wang, Huddinge (SE)

( * ) Notice: Subject to any disclaimer, the term of this patent is extended or adjusted under 35 U.S.C. 154(b) by 448 days.

(21) Appl. No.: 18/001,109

(22) PCT Filed: Jun. 8, 2021

(86) PCT No.: PCT/SE2021/050547
§ 371 (c)(1),
(2) Date: Dec. 8, 2022

(87) PCT Pub. No.: WO2021/251882
PCT Pub. Date: Dec. 16, 2021

(65) Prior Publication Data
US 2023/0211148 A1    Jul. 6, 2023

(30) Foreign Application Priority Data

Jun. 9, 2020 (SE) .................................. 2030191-7

(51) Int. Cl.
*A61N 1/04* (2006.01)
*A61N 1/30* (2006.01)
(52) U.S. Cl.
CPC ......... *A61N 1/0456* (2013.01); *A61N 1/0476* (2013.01); *A61N 1/30* (2013.01)

(58) Field of Classification Search
None
See application file for complete search history.

(56) References Cited

U.S. PATENT DOCUMENTS

| 9,616,221 B2 | 4/2017 | Gross |
| 2014/0032412 A1 | 1/2014 | Park et al. |

(Continued)

*Primary Examiner* — Michael W Kahelin
(74) *Attorney, Agent, or Firm* — Renner, Otto, Boisselle & Sklar, LLP

(57) ABSTRACT

The present invention relates to a method for inducing a controlled fluid transport in a central nervous system, CNS, and/or in a cerebrospinal fluid, CSF system, of a patient by electro-osmosis, EO, via two or more electrodes placed at selected locations on the patients head, comprising receiving EO information, the EO information being at least indicative of fluid transport response resulting from application of particular electric potentials and/or currents at particular electrode locations on the patient's head based on a patient-specific three-dimensional head model, receiving a fluid source location within the patient's head, selecting a set of electrode locations using the EO information and the fluid source location, placing the two or more electrodes in electrical communication with said CNS/CSF-system, each electrode being placed at one location of the selected set of electrode locations, and controlling an application of selected electric potentials and/or electric currents to said electrodes, wherein the selected electric potentials and/or electric currents is selected as electric potentials and/or electric currents associated to the selected set of electrode locations by the EO information, so as to induce a controlled fluid transport in said CNS/CSF-system.

21 Claims, 9 Drawing Sheets

(56) References Cited

U.S. PATENT DOCUMENTS

2017/0274207 A1    9/2017  Gross
2019/0076653 A1*   3/2019  Fostick .............. A61N 1/36082

* cited by examiner

TREATMENT DEVICE

This application is a national phase of International Application No. PCT/SE2021/050547 filed Jun. 8, 2021, which claims priority to Swedish Application No. 2030191-7 filed Jun. 9, 2020, each of which is hereby incorporated herein by reference in its entirety.

TECHNICAL FIELD

The invention relates to a method, a device, a computer program module and a system for the treatment of a central nervous system and/or a cerebrospinal fluid system. In particular, the invention relates to inducing a fluid transport in said systems by electro-osmosis.

BACKGROUND

Cerebral edema is defined as an increased amount of water content in the nervous tissue, which is a major neurological complication of traumatic brain injury and stroke. Raised intracranial pressure is found in most patients with cerebral edema and the patients may deteriorate unless treated effectively.

At present, cerebral edema is often treated with corticosteroid or osmotic diuretic agents. Especially, osmotherapy has been regarded as the mainstay of pharmacologic therapy, which however may cause side effects such as acute renal failure and decreased cerebral perfusion. Further, when the mass effect of cerebral edema is too high to be controlled by osmotherapy treatment alone, neurosurgical treatment (e.g., decompressive craniotomy) is the ultimate choice for patients with most severe traumatic brain injury and stroke aiming at reducing intracranial pressure caused by cerebral edema. Decompressive craniotomy indeed reduces mortality but increases survival with severe disability and some patients are left in a vegetative state, which may be attributed to the severe stretching of brain tissue at both the inner brain and bony edges.

Therefore, although improvements in outcome have been presented during the last decades, cerebral edema and raised intracranial pressure are still without any distinct and successful treatment. The central nervous system and/or a cerebrospinal fluid system is sensitive to an excess build-up of fluid, such as but not limited to cerebral edema, that may damage the system. An efficient method to remove or alleviate such fluid build-up is needed.

In US 2014/032412 and US2017/0274207, a method is shown to drive fluid electroosmotically for the treatment of hydrocephalus. In this patent, two insulated electrodes are implanted in the brain to drive fluid flow electroosmotically between the first and second electrodes based on capacitance-based current. This invasive method by implanted electrodes has the disadvantage of increasing the risks associated with implantation and operation of the system, and potentially cause secondary damage to the brain near the implanted electrodes. Besides, the induced fluid flow is driven by capacitance-based current using insulated electrodes. The disadvantage is the uncertainty in the effectiveness and efficiency due to the capacitance-based current induced by insulated electrodes, especially for inducing fluid flow to move fluids over a longer distance than a few centimeters.

US2019/0076653 describes a method to treat the accumulation of substances such as amyloid beta and/or tau protein in the brain with three electrodes. In this patent, the substance is driven from the brain parenchyma into the cerebrospinal fluid-filled space of the brain, and then to the superior sagittal sinus based on principles of electrophoresis and electroosmosis. Direct current is applied with an average amplitude of at least 1 mA and no more than 5 mA, or an average amplitude of less than 1.2 V. However, the invasive method by implanted electrodes has the disadvantage of potentially causing secondary damage to the brain near the implanted electrodes. Besides, such an amplitude may cause electrolysis around the implanted electrodes which can damage the brain.

In U.S. Pat. No. 9,616,221, a method is described to treat subjects identified as at risk of or suffering from Alzheimer's disease by electroosmotically driving fluid from a subarachnoid space to the superior sagittal sinus. The midplane treatment electrodes are disposed over the superior sagittal sinus, and lateral treatment electrodes are disposed between 1 and 12 cm of a sagittal midplane of the skull. However, such an electrode configuration is used to drive fluid flow from the subarachnoid space to the superior sagittal sinus. It will therefore only have a minimal effect on the superficial gray matter of the brain and will have a negligible effect on the deeper white matter. The disadvantage of having the treatment electrodes at fixed locations rather than at particular electrode locations based on the fluid source location within the patient's head is a lack of controlled fluid transport in the central nervous system, and/or in the cerebrospinal fluid system.

Moreover, none of the prior art specify crucial information affecting electro-osmosis such as fluid transport response resulting from application of particular electric potentials and/or currents at particular electrode locations on the patient's head or the fluid source location within the patient's head, which are all critical parameters to induce a controlled fluid transport in a central nervous system, and/or in a cerebrospinal fluid system of a patient by electro-osmosis. Thus, an improved and non-invasive method for controlling or modulate fluid flow in the central nervous system, and/or in a cerebrospinal fluid system is needed which has wide applications for the treatment of a variety of neurological diseases, such as but not limited to the treatment of cerebral edema at various locations (localized and diffuse).

Especially for edema treatment, such a method can be used as complementarity in the treatment of patients with decompressive craniotomy surgery to reduce the magnitude and duration of edema thus to improve patient outcome. Further, such a method can be used as a new non-invasive therapy to remove extra edematous fluid to avoid decompressive craniotomy; or to be a complementarity to the limited treatment of choice currently available for patients with moderate or minor cerebral edema.

SUMMARY OF THE INVENTION

The above mentioned and other problems may be alleviated by the use of a method, a device, a computer program module, or a system according to any of the appended claims.

According to a first aspect of the invention, there is provided a method for inducing a controlled fluid transport in a central nervous system, CNS, and/or in a cerebrospinal fluid, CSF, system, of a patient by electro-osmosis, EO, via two or more electrodes placed at selected locations on the patients head, the method comprising receiving EO information, the EO information being at least indicative of fluid transport response resulting from application of particular electric potentials and/or currents at particular electrode locations on the patient's head based on a patient-specific three-dimensional head model, receiving a fluid source location within the patient's head, selecting a set of electrode locations using the EO information and the fluid source location, placing the two or more electrodes in electrical communication with said CNS/CSF-system, each electrode being placed at one location of the selected set of electrode locations, and controlling an application of selected electric potentials and/or electric currents to said electrodes, wherein the selected electric potentials and/or electric currents is selected as electric potentials and/or electric currents associated to the selected set of electrode locations by the EO information, so as to induce a controlled fluid transport in said CNS/CSF-system.

According to a second aspect of the invention, there is provided a method for inducing a controlled fluid transport in a central nervous system (CNS) and/or in cerebrospinal fluid (CSF) system by electro-osmosis. The method comprises:
- a) receiving information on electrode location and/or on electrode potentials and/or electrode currents selected to achieve a controlled fluid transport in said CNS/CSF-system, wherein the information is generated by a computer simulation of induced fluid transport in a computer model of said CNS/CSF-system, the computer model being generated based on a set of image scans of the CNS/CSF-system and the simulation being performed by simulating the fluid transport response from applying electric potentials and/or currents via at least one simulated anode and at least one simulated cathode placed in electrical communication with said CNS/CSF-system in said computer model,
- b) placing at least two electrodes in electrical communication with said CNS/CSF-system, and
- c) controlling with a control unit an application of electric potentials and/or electric currents to said electrodes based on the received information from the computer simulation, so as to induce a controlled fluid transport in said CNS/CSF-system.

Preferably, the method comprises placing at least one electrode acting as a cathode and at least one electrode acting as anode at locations corresponding to the locations of simulated cathodes/anodes. Preferably, the method comprises applying an electric potential and/or electric current to electrodes placed at locations corresponding to the locations of simulated cathode/anodes. Preferably, the method comprises applying electric potential(s) and/or electric current(s) to electrodes, corresponding to simulated electric potential(s) and/or electric current(s) applied to simulated electrodes. Preferably, the method comprises controlling an application of electric potentials and/or electric currents to said electrodes in accordance with at least one simulation result in the received information from the computer simulation.

According to one embodiment, the method comprises selecting a region of the CNS/CSF-system that is to be drained of fluid and selecting a region of the CNS/CSF-system that is to receive fluid, and that method step b) comprises:
- b1) placing at least one cathode in electrical communication with the CNS/CSF-system in a position behind the region that is to receive fluid, as viewed from the region that is to be drained of fluid, and
- b2) placing at least one anode in electrical communication with the CNS/CSF-system in spaced-apart positions behind the region that is to be drained of fluid, as viewed from the region that is to receive fluid.

Preferably the region to receive a fluid is a ventricle, such as a cerebrospinal fluid ventricle, such as a lateral ventricle in a brain, and/or a superior sagittal sinus. In one embodiment, the method comprises selecting a pathway region of the CNS/CSF-system. The pathway region preferably comprises a region located between the region to be drained of fluid and the region to receive the fluid, and which form a preferred pathway for fluid flow between the two latter regions. In one embodiment, the method comprises selecting side regions, which are located beside the region to be drained, the pathway region, and the region to receive fluid.

In one embodiment, the method comprises selecting regions of the CNS/CSF-system in which fluid flow and/or fluid accumulation should be avoided. In one embodiment, the side region and the regions in which fluid flow and/or fluid accumulation should be avoided coincide.

In one embodiment the method step c) comprises:
- c1) controlling with a control unit the application of electric potential and/or electric current to at least one cathode and to at least one anode so as to focus a fluid transport from a region selected to be drained of fluid towards a region selected to receive fluid.

By focusing the fluid flow, it allows avoiding accumulation of fluid above a threshold value that would risk harming a tissue, and/or a fluid flow above a threshold value that would risk harming a tissue, in regions of the biological tissue in which a fluid transport is to be avoided. Thus, a fluid transport from the region to be drained into a region for receiving the fluid is focused to the selected pathway, and so as to impede a secondary fluid flow or transport into a side region or into a region into which fluid flow is to be avoided.

A more complete understanding of embodiments of the invention will be afforded to those skilled in the art, as well as a realization of additional advantages thereof, by a consideration of the following detailed description of one or more embodiments. It should be appreciated that like reference numerals are used to identify like elements illustrated in one or more of the figures.

Figure 1:
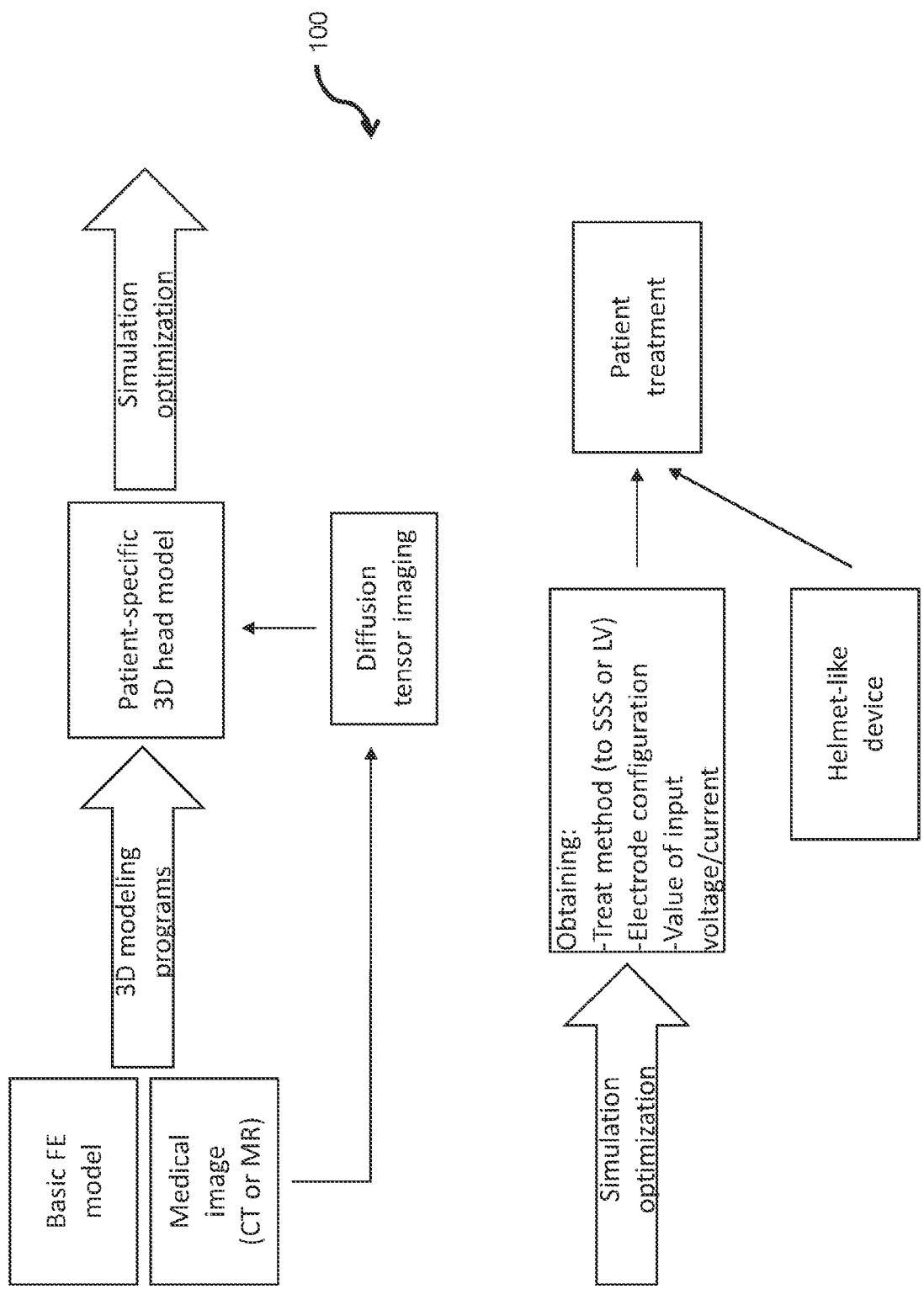
FIG. 1 shows the patient-specific treatment process of the invention.

A more complete understanding of embodiments of the invention will be afforded to those skilled in the art, as well as a realization of additional advantages thereof, by a

DETAILED DESCRIPTION

In the present disclosure, the term "glymphatic flow" denotes fluid flow in the glymphatic system and/or glymphatic clearance pathway and/or the para vascular system.

In the present disclosure, the term "modulating the glymphatic flow" denotes changing/modifying the direction or velocity of the glymphatic flow and may be used interchangeably with "modifying the glymphatic flow" or "changing the glymphatic flow".

In the present disclosure, the term "electro-osmosis" may be used interchangeably with electroosmotic flow, electroosmotic flow, electroosmosis or electroendosmosis and denotes the motion of fluid induced by an applied potential across a porous material or any other fluid conduit.

In the present disclosure, the term "patient-specific three-dimensional head model" denotes a model capable of providing a fluid transport response given input parameters, such as selected electric potentials and/or currents applied at selected electrode locations on the patients head. In other words, the fluid transport response represents a controlled fluid transport in said CNS/CSF-system. In the present disclosure, the term "computer model", "computer model of said CNS/CSF-system" and "patient-specific three-dimensional head model" are used interchangeably. The patient-specific three-dimensional head model may comprise models of how various parts of the patient's head reacts to the given input parameters, e.g. model of a fiber structure within the CNS/CSF-system, model of the skin, model of the skull bone, model of body membranes, model/information on damaged nervous tissue and healthy nervous tissue, model of the brain, model of cerebrospinal fluid, model of brain ventricles, model of white brain tissue, model of gray brain tissue, model of a brain stem, model of the spinal cord. The models may e.g. include values of electric material parameters, such as electric conductivity and/or dielectric constants.

In the present disclosure, the term "image scans" denotes output/results from imaging systems used on and targeting the patient's head, such as a set of Computed Tomography, CT, image scans and/or a set of multimodal medical image scans, such as Magnetic Resonance Imaging, MRI, image scans and/or ultrasound image scans and/or Positron Emission Tomography, PET, image scans.

In the present disclosure, the term "behind", when used to describe positioning of electrodes, denotes a relative location along a surface of the patient's head. In other words, at a location where a straight line originating from a fluid target location, such as the superior sagittal sinus, via a fluid source location, such as an edema, intersects the surface of the patient's head.

According to one aspect, the present invention relates to fluid disorder, such as edema, treatment based on tissue's electroosmotic property which allows directing of edematous fluid when electrodes are applied to the head of a patient.

We provide a technical solution which in some embodiments use a helmet-like medical device developed for edema treatment (FIG. 2). The helmet-like device provides application of particular electric potentials and/or currents at particular or predefined electrode locations on the patient's head.

The mechanisms behind the present invention are the electroosmotic property of the brain: Electroosmotic flow can be induced by electric field when applying electrodes. By activating the electrodes in a designed manner, the present disclosure can treat edema of different types at various locations including localized brain edema and diffused brain edema and is expected to work for various types of edema including vasogenic and cytotoxic. The present disclosure can also be used to modify/modulate glymphatic flow. The disclosure allows focalized treatment by targeting the required tissue area and direct fluid along the preferred paths to avoid unnecessary disturbance in an otherwise relatively healthy brain by activating electrodes based on the simulation results of a patient-specific three-dimensional head model. For patients with localized edema, the fluid in edematous tissue may e.g. be directed either to the superior sagittal sinus, where cerebrospinal fluid is absorbed, or to the lateral ventricle to the cerebrospinal fluid circulation. For patients with diffused edema, the fluid in edematous tissue may e.g. be directed to the superior sagittal sinus. For patients with expanded brain due to the opening of skull bone in decompressive craniotomy, the helmet-device is not applicable. Instead, a new design is proposed to apply electrode at selected electrode locations to the dura mater directly and the fluid in edematous tissue may e.g. be directed to superior sagittal sinus.

Figure 2A:
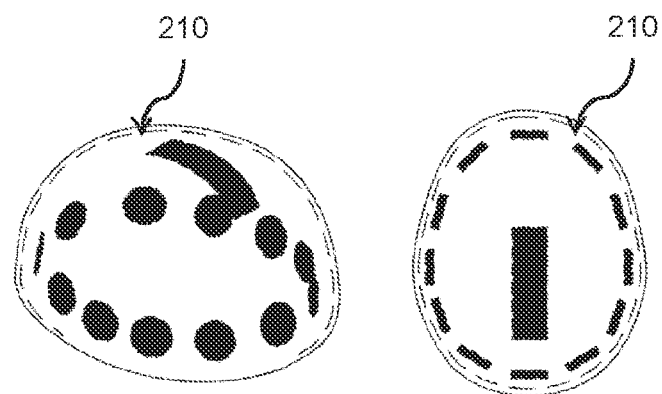
FIG. 2A-E shows various devices for treatment according to aspects of the invention.
Figure 2B:
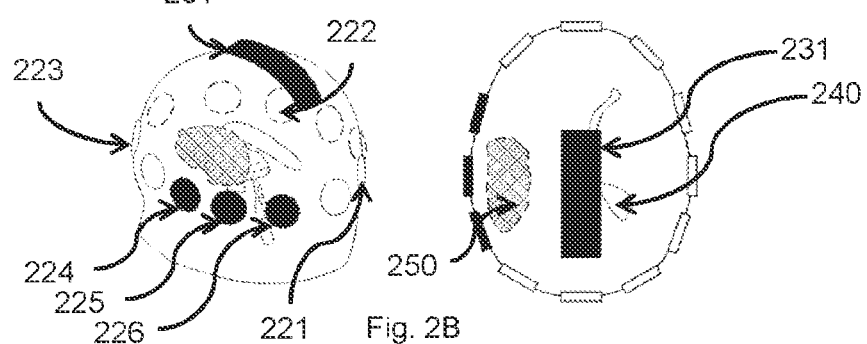
Figure 2C:
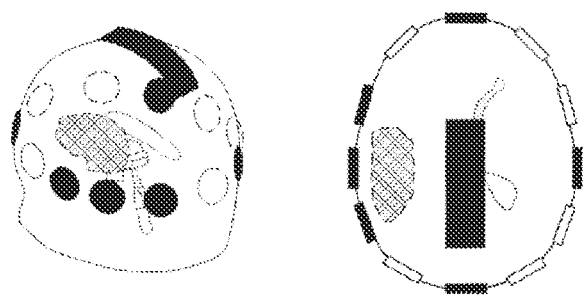
Figure 2D:
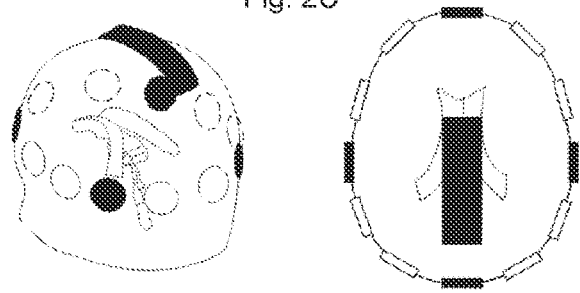
Figure 2E:
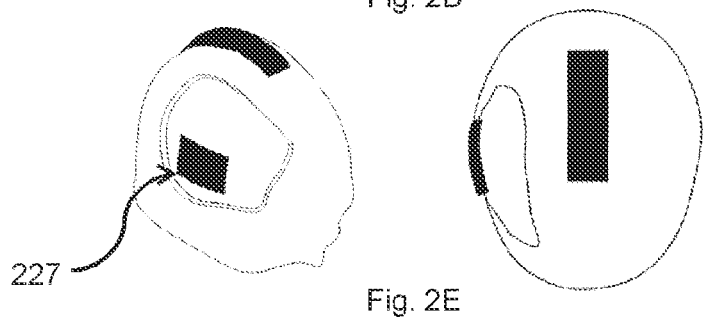

The use of the cathode/anode-helmet-like device 210 for edema treatment is illustrated in FIG. 2A. FIG. 2B illustrates an application of the disclosure for fluid transport from a localized edema 250 to the superior sagittal sinus. FIG. 2C illustrates an application of the disclosure for fluid transport from a localized edema to the ventricle. FIG. 2D illustrates an application of the disclosure for fluid transport from the diffuse edema to the superior sagittal sinus. FIG. 2E illustrates an application of the disclosure for fluid transport from a localized edema with decompressive craniectomy to the superior sagittal sinus.

Three patients, #1-#3, are used to demonstrate the concept. Activated electrodes to treat localized brain edema by directing to superior sagittal sinus and ventricle (FIGS. 2B&C) is exemplified with patient #1 shown in FIGS. 3&4, respectively. Activated electrodes to treat diffuse brain edema by directing to superior sagittal sinus (FIG. 2D) is exemplified with patient #2 shown in FIG. 5. Activated electrodes to treat localized brain edema by directing to superior sagittal sinus (FIG. 2E) for an expanded brain is exemplified with patient #3 shown in FIG. 6.

FIG. 2A-D show different views of a helmet-like device 210 (FIG. 2A) for edema treatment capable of both localized edema 250 (FIGS. 2B and 2C) and diffuse edema treatment (FIG. 2D) by activating the designed electrodes.

In FIG. 2A-2D, activated electrodes are illustrated by hatching and non-active electrodes are illustrated as blank or non-filled. In one example (FIGS. 2B and 2D), the electrodes illustrated with a circular shape may be anode electrodes and the electrode illustrated with rectangular shape may be a cathode electrode. In one example (FIG. 2C), the electrodes illustrated with a circular shape may be anode electrodes and cathode electrodes.

A separate design is made for expanded brains where it is not suitable to use a helmet and is illustrated in FIG. 2E.

According to one aspect, the invention includes a method for edema treatment by applying electrode utilizing tissue's electroosmotic property and based on patient CT image, comprising:

a) obtaining CT images of the patient brain;
b) generation of a patient-specific three-dimensional model of the patient head based on the CT images, including edema component, and computer simulations simulating it with helmet-like device;
c) selecting the reasonable electrodes to be activated based on the simulation results of the patient-specific three-dimensional model;
d) installing the helmet-like device on patient head and activating the selected electrodes to drive the edematous fluid to flow from edema region to superior sagittal sinus or lateral ventricle.

According to one embodiment, a cap/helmet-like device provided with electrodes located at predetermined positions is designed to be activated using different selected electrodes according to the required target from patient CT image. The cap/helmet-like device comprises a plurality of electrodes. The cap/helmet-like device may e.g. include 13 electrodes, a control unit, and cap/helmet-like shell or mechanically connected body. The configurations of electrodes as anode and cathode electrode (e.g. distance and required voltage) are determined based on the patient-specific three-dimensional head model. An electrode, e.g. a rectangular electrode, is applied to the dura, and another rectangular electrode is applied to the superior sagittal sinus, for patients with expanded brain due to opening of skull bone in decompressive craniotomy. The treatment focality is controlled by adjusting the location of the electrodes based on the simulation results or fluid transport response of the patient-specific three-dimensional head model. When using the helmet-like device this includes selecting which electrodes to activate as anode and/or cathode electrodes. Integrating diffusion tensor imaging (DTI) during the numerical simulation of the patient-specific three-dimensional head model will improve the accuracy of treatment focality. The method can be used to treat localized and diffuse edema, and applicable to post-craniotomy patient.

Figure 3:
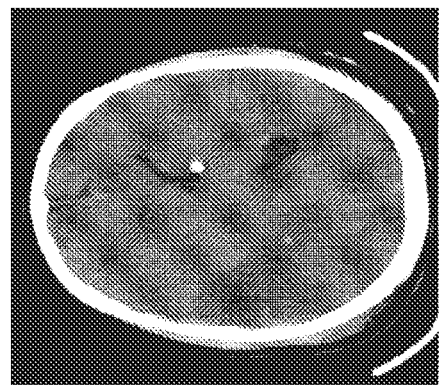
FIG. 3 shows image scans of Patient #1, computer simulation results, and device according to aspects of the invention.
Figure 3:
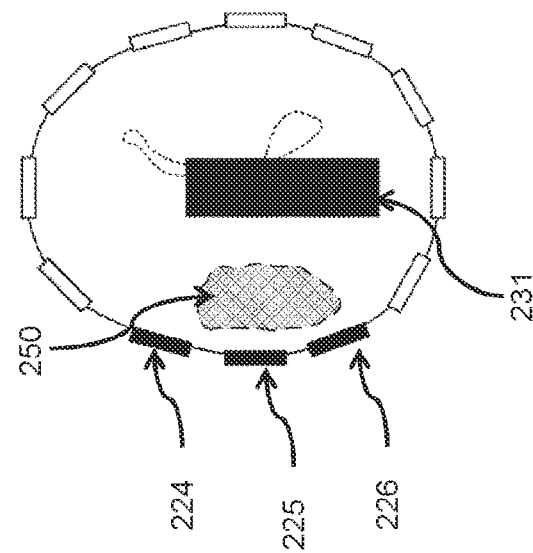
Figure 3:
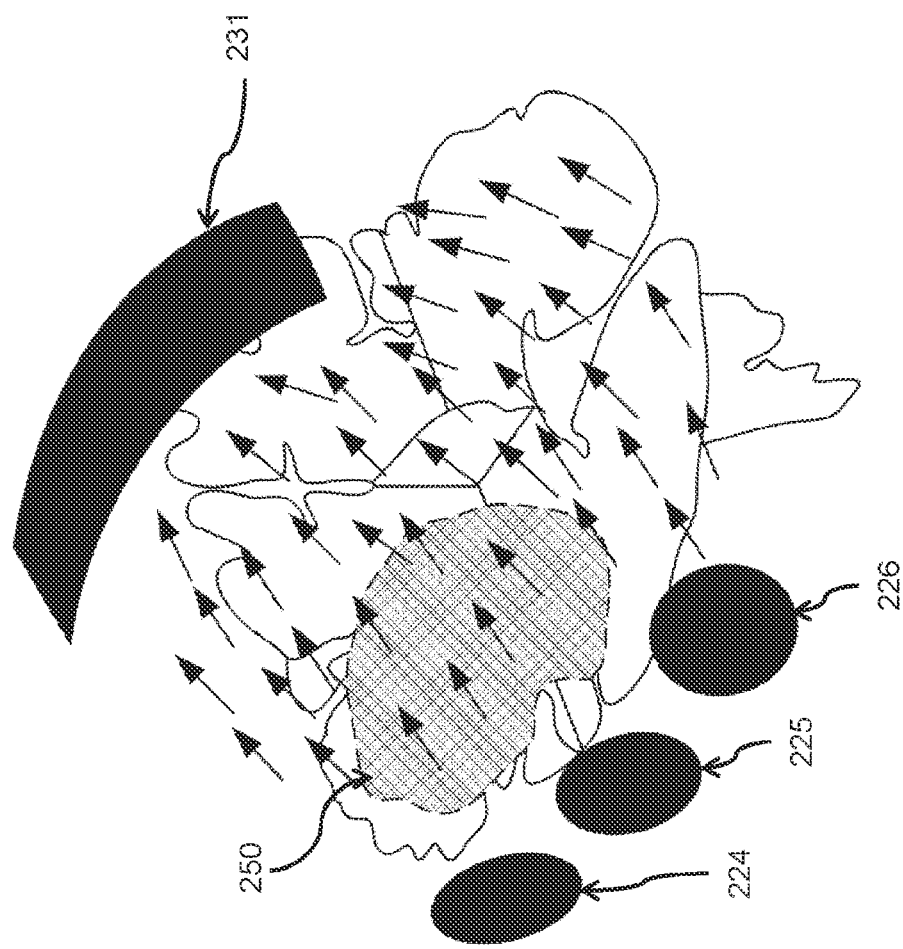

FIG. 3 shows a Patient #1 CT image 310 with localized brain edema, which is used to generate a patient-specific head model with edema included (right column). Anode electrodes 224-226 and cathode electrode 231 are activated to direct edematous tissue fluid to the superior sagittal sinus (left column).

Figure 4:
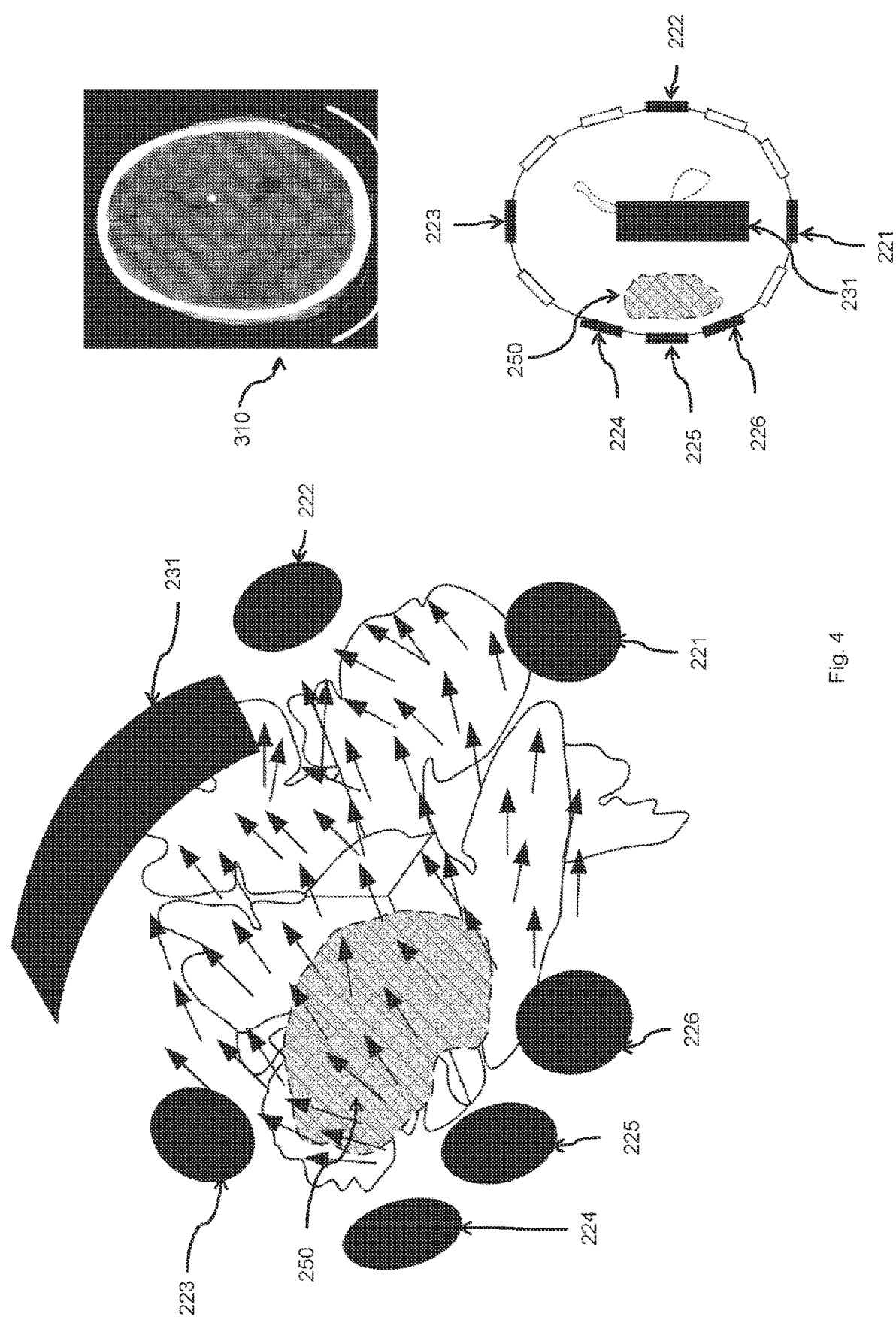
FIG. 4 shows further image scans of Patient #1, computer simulation results, and device according to aspects of the invention.

FIG. 4 shows a Patient #1 CT image 310 showing localized brain edema, which is used to generate a patient-specific head model with edema included (right column). Anode electrodes 224-226 and cathode electrodes 221-223 are activated to direct edematous tissue fluid to the ventricle (left column).

Figure 5:
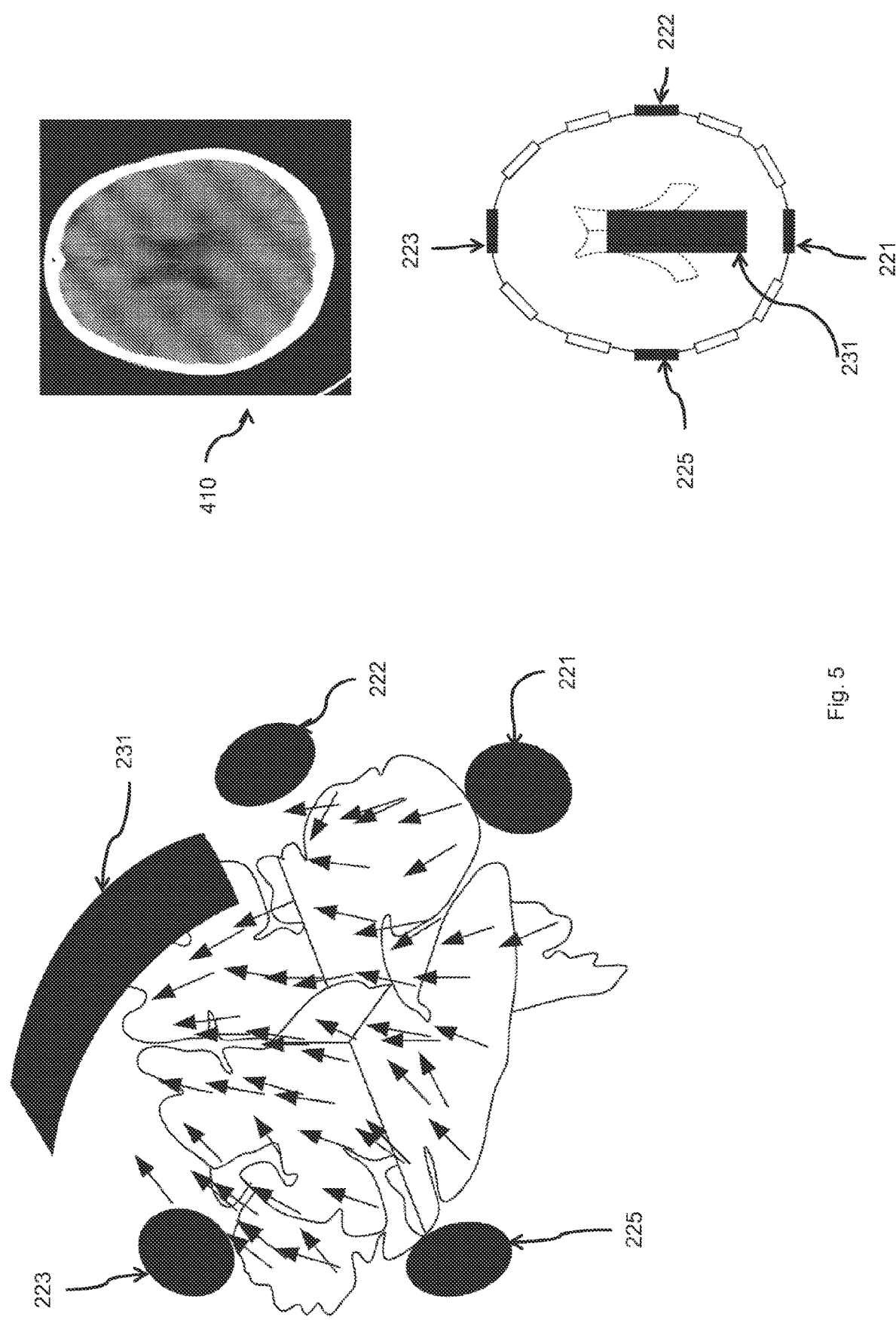
FIG. 5 shows further image scans of Patient #2, computer simulation results, and device according to aspects of the invention.

FIG. 5 shows a Patient #2 CT image 410 showing diffuse brain edema, which is used to generate a patient-specific head model with edema included (right column). Anode electrodes 221-223, 225 and cathode electrodes 231 are activated to direct edematous tissue to the superior sagittal sinus (left column).

Figure 6:
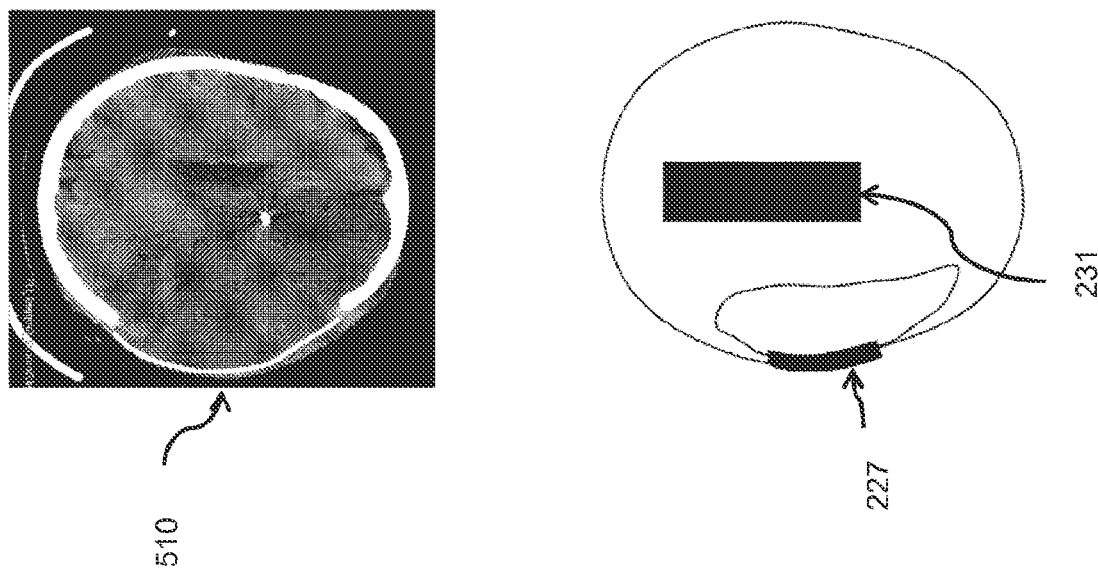
FIG. 6 shows further image scans of Patient #3, computer simulation results, and device according to aspects of the invention.
Figure 6:
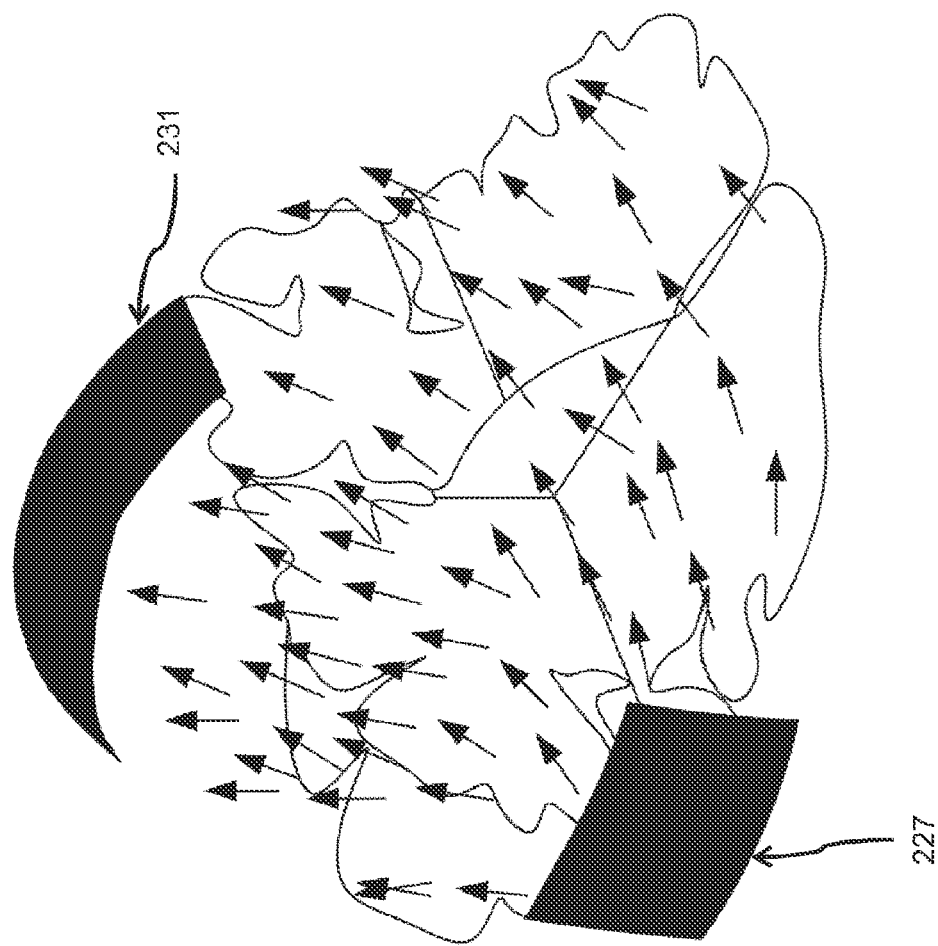

FIG. 6 shows a Patient #3 that went through a decompressive craniotomy surgery by opening the skull bone to let the brain expand outside the skull bone to release intracranial pressure. The CT image 510 is used as input to generate a patient-specific head model with expanded brain (right column). Anode electrode 227 is applied to the dura surface to direct the edematous tissue fluid to the superior sagittal sinus (left column).

Figure 7D:
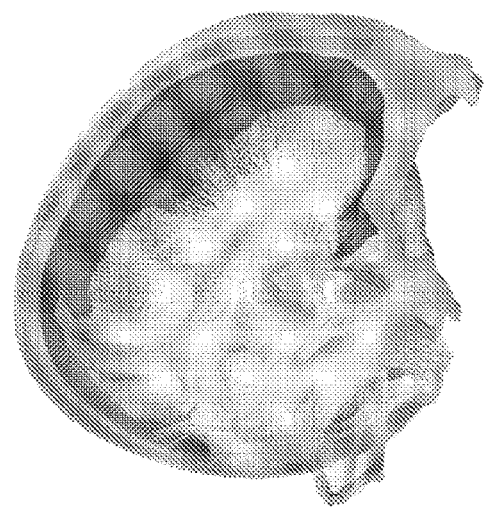
FIG. 7 shows computer simulations and computer models of CNS/CSF-system, especially taking fiber direction into account.
Figure 7C:
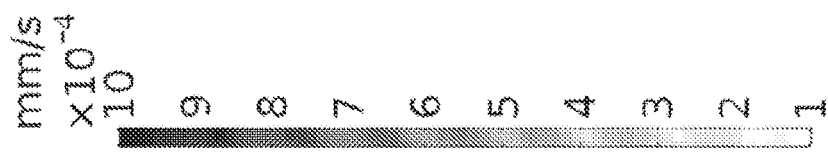
Figure 7B:
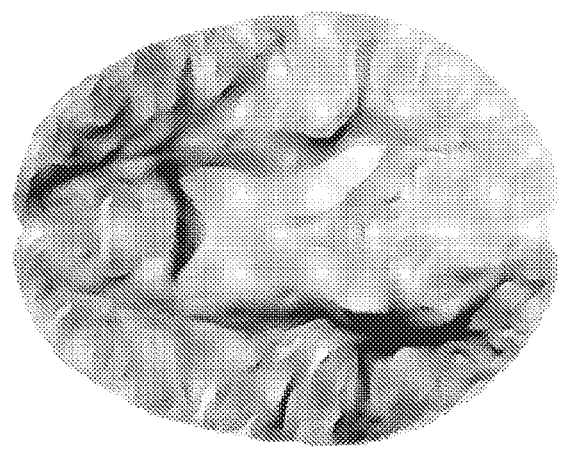
Figure 7A:
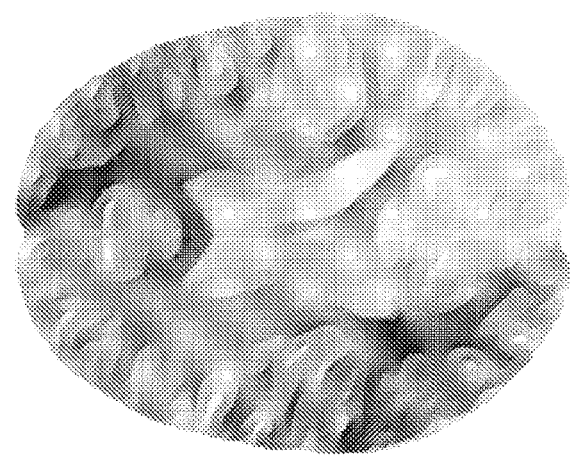

FIG. 7A-7D shows examples to illustrate how DTI allows better optimization of the fluid flow path. FIG. 7A illustrates when fiber direction is not accounted for in the simulation. FIG. 7B illustrates a better optimization of fluid flow is allowed by accounting for fiber direction in the model. FIG. 7C illustrates the electroosmotic fluid flow velocity value. FIG. 7D illustrates when fiber direction is accounted for in the simulation by including DTI information to the model. The fluid flow is shown to move faster along the fiber direction and slower perpendicular to the fiber direction.

According to one embodiment, there is a method for inducing a controlled fluid transport in a central nervous system (CNS) and/or in a cerebrospinal fluid (CSF) system by electro-osmosis, comprising:
a) receiving information on electrode location and/or on electrode potential and/or electrode current selected to achieve a controlled fluid transport in said CNS/CSF-system, wherein the information is generated by a computer simulation of an induced fluid transport in a computer model of said CNS/CSF-system, the computer model being generated based on a set of image scans of the CNS/CSF-system and the simulation being performed by simulating the fluid transport response from applying electric potentials and/or currents via at least one simulated anode and at least one simulated cathode placed in electrical communication with said CNS/CSF-system in the said computer model,
b) placing two or more electrodes, anode and/or cathode electrodes, in electrical communication with said CNS/CSF-system, and
c) controlling with a control unit an application of electric potentials and/or electric currents to said electrodes based on the received information from the computer simulation, so as to induce a controlled fluid transport in said CNS/CSF-system.

According to one embodiment, the invention includes placing two or more electrodes in electrical communication with said part of the CNS at positions which to more than 50% conform with the positions of the corresponding, simulated electrodes in the said computer model. According to one embodiment, the invention includes placing the electrodes at positions which to more than 70% conform with the positions of the simulated electrodes.

According to one embodiment, the invention includes placing the electrodes at positions which to more than 85% conform with the positions of the simulated electrodes. According to one embodiment, the invention includes placing the electrodes at positions which to more than 90% conform with the positions of the simulated electrodes. According to one embodiment, the invention includes placing the electrodes at positions which to more than 95% conform with the positions of the simulated electrodes. Adding more electrodes allows for better and more fine-tuned control of a resulting electric field and/or a resulting current within the CNS/CSF-system. It also allows for a higher probability that an electrode is present at a desired location, in case electrodes are provided in fixed positions on a device to be placed on the CNS/CSF-system.

According to one embodiment, the method/device/system includes controlling said electric potentials and/or electric currents so that electrodes placed in positions conforming with simulated anodes act as anodes, and so that electrodes placed in positions conforming with simulated cathodes act as cathodes. According to one embodiment, the computer model comprises at least four simulated electrodes, of which at least three electrodes are designated to act as anodes, and at least one electrode is designated to act as a cathode, and that the method step d) includes placing at least four electrodes in electrical communication with said part of the CNS, of which at least three electrodes act as anodes and at least one electrode act as cathode. According to one embodiment, the method/device system includes at least two electrodes, and at least one electrode is designated to act as cathode, and at least one electrode is designated to act as anode.

According to one embodiment, the individual to be treated is an animal belonging to the vertebrae family. According to one embodiment, there is an individual having a central nervous system (CNS) and/or cerebrospinal fluid (CSF)-system to be treated. For example, the central nervous system may have sustained a damage. According to one embodiment, the individual to be treated is a human.

According to one embodiment, the term 'is in electrical communication with' means that at least one-tenth of an electric field emanating from an electrode penetrates into the tissue with which it electrically communicates. Alternatively, the term electrical communication may mean that at least one-tenth of a current emanating from an electrode penetrates into the tissue with which it electrically communicates. Preferably, at least one-third of the field strength and/or current penetrates into the tissue, alternatively at least 50% of the field strength or current penetrates into the tissue. Alternatively, the term electrical communication may mean that an applied potential or current have the ability to affect the fluid transport in the CNS/CSF-system at levels giving therapeutic effect. Alternatively, the term electrical communication means that the applied potential or current have the ability to cause a fluid flow density of at least I nl/min*cm$^2$ due to electro-osmosis. Preferably, the method includes placing the electrodes on an individual in electrical communication with a CNS/CSF-system of the individual.

According to one embodiment, the method comprises selecting a region of the CNS/CSF-system that is to be drained of fluid, and selecting a region of the CNS/CSF-system that is to receive fluid, and that method step b) comprises:
  b1) placing at least one cathode in electrical communication with the CNS/CSF-system in a position behind the region that is to receive fluid, as viewed from the region that is to be drained of fluid, and
  b2) placing at least one anode in electrical communication with the CNS/CSF-system in spaced-apart positions behind the region that is to be drained of fluid, as viewed from the region that is to receive fluid.

According to one embodiment the method comprises in step c):
  c1) controlling with a control unit the application of electric potential and/or electric current to at least one cathode and to at least one anode so as to focus a fluid transport from a region selected to be drained of fluid towards a region selected to receive fluid.

Preferably, the method includes placing at least one first anode to at least partly cover a region of the CNS that is to be drained, and at least one second anode to at least partly cover a side region that is located beside the region to be drained, wherein the first and second anodes constitute said first and second anode parts, respectively. Preferably, the method includes independently applying electric potentials and or electric currents to the first and second anodes. In one embodiment, the first and second electrodes are supplied with different potential/current strengths. This allows fine-tuning of the fluid flow to an intended pathway for the fluid. According to one embodiment, the method includes placing at least one first anode to at least partly cover a region of the CNS that is to be drained of fluid, and placing at least a second and a third anode to at least partly cover a side region located beside the region to be drained. This allows stopping a fluid flow from entering the side region. Preferably, at least one anode is placed so that an electric field and/or current emanating from the anode penetrates into the region to be drained of fluid, so to allow electro-osmosis and a fluid flow out of the region to be drained.

According to one embodiment said image scans are one of CT-image scans, PET-image scans and/or MR-image scans. According to one embodiment, the set of image scans is a set of CT-image scans.

According to one embodiment, the method/computer program module further comprises:
  a1) receiving in a computer memory at least one set of image scans of the CNS/CSF-system,
  a2) generating a computer model of said CNS/CSF-system based on the received set of image scans, and
  a3) simulating with a computer a fluid transport in the computer model of said CNS/CSF-system in response to applying electric potentials and/or currents via at least one simulated anodes and at least one simulated cathode placed in electrical communication with said CNS/CSF-system.

In one embodiment, the method also comprises obtaining the CT-image scan from the individual to be treated. Preferably, the method includes performing several simulations based on the same model of an individual, using various locations for the electrodes and/or various applied potentials to the electrodes. This allows selecting a pathway for the fluid flow giving a high fluid transport towards the receiving region. It may also allow selecting a pathway for the fluid flow that may avoid damaging tissue. It may also allow selecting a pathway for the fluid flow that avoids a secondary fluid flow into side regions. Preferably, the simulation simulates an induced fluid transport within the CNS/CSF-system via electro-osmosis, obtained by applying electric potentials and/or currents resulting in an electric field. Such electric field and/or current may drive a fluid flow by process of electro-osmosis. Preferably, the method includes controlling the fluid flow by utilizing electro-osmosis induced fluid flow using said electrodes.

In one embodiment, said computer model/patient-specific three-dimensional head model includes a 3D-model of a CNS/CSF-system. In one embodiment, said computer model of the CNS/CSF-system includes information on a fiber structure within the CNS/CSF-system. The fiber structure within brain tissue may divert fluid flow from the direction of an applied electric field in the direction of fiber. By including a fiber structure with the computer model used for simulating the fluid flow, such fiber structure may be taken into account. According to one embodiment, said computer model includes a model of skin. According to one embodiment, said computer model includes a model of bone. Preferably, said computer model includes values of electric material parameters, such as electric conductivity and/or dielectric constants. According to one embodiment, said computer model includes a model of body membranes. Preferably, said computer model includes values of fluidic material parameters, such as membrane permeability. Preferably, said computer model includes values of osmotic parameters, such as salinity and/or osmotic pressure. Preferably, said simulation step c) includes simulating osmotic pressure. According to one embodiment, said computer model comprises information on damaged nervous tissue and on healthy nervous tissue. Damaged and healthy nervous tissue may have different material parameters, which situation can be simulated in the model. Preferably, the method includes identifying and classifying damaged nervous tissue and healthy nervous tissue from a CT-image scan. Alternatively, the method may include receiving information on damaged nervous tissue and healthy nervous tissue. According to one embodiment, said computer model includes a 3D-model of a brain, of cerebrospinal fluid, of brain ventricles, of skull bone and of scalp. In one embodiment, said computer model of said part of the CNS/CSF-system includes a model of white brain tissue and of gray brain tissue. In one alternative embodiment, said computer model includes a model of a brain stem and/or part of a spinal cord, and of neighboring bone.

According to one embodiment, the method includes placing one or more anodes in a position behind the region to be drained, as viewed from the region to receive the fluid. According to one embodiment said CNS/CSF-system is afflicted with edema, and the method comprises selecting the edema 250 as a region to be drained of fluid,
simulating a fluid transport in a direction away from the edema, and
controlling the fluid transport and the application of electric potentials and/or electric currents to said electrodes so as to control fluid transport away from the edema.

Thus, the edema is the region to be drained of fluid. According to one embodiment, the method includes placing at least one first anode part to cover the edema, and at least one second anode part to cover a side region located beside the edema. Preferably, the method includes controlling the fluid transport and the application of electric potentials and/or electric currents so as to drive at least one fluid towards a natural drain channel. The fluid may be blood, cerebrospinal fluid or spinal fluid. Preferably, the method includes controlling a fluid transport in said individual in a direction from edema and into the CSF-system. According to one embodiment said CNS/CSF-system includes a brain afflicted with edema, and the method includes controlling the fluid transport so as to drive at least one fluid away from the edema and towards a lateral brain ventricle and/or towards a superior sagittal sinus. Alternatively, said part of the CNS includes a brain stem and/or part of a spinal cord afflicted with edema, and the method includes controlling the fluid transport so as to drive at least one fluid away from the edema and towards a spinal channel.

According to one embodiment, the method includes placing a device comprising a mechanically connected body and at least four spaced-apart electrodes in electrical communication with the CNS/CSF-system to be treated, e.g. a helmet-like device with electrodes to be placed at predetermined locations/positions on the mechanically connected body.

According to one embodiment, the method includes placing a device comprising a mechanically connected body and at least four spaced-apart electrodes onto a CNS/CSF-system to be treated. In one embodiment, the method includes placing the device onto a vertebra. In one embodiment, the method includes placing the device onto an animal. In one embodiment, the method includes placing the device onto an individual. In one embodiment, the method includes placing the device onto a human. In one embodiment, the method includes placing the device onto a patient. In one embodiment, the method includes in step d) placing a device comprising at least one anode and at least one cathode in fixed designated positions onto said part of the CNS/CSF-system to be treated.

According to one embodiment, that method includes placing a device onto a CNS/CSF-system, and the device is a net, a cap or a helmet configured to fit onto a head of an individual to be treated. Alternatively, the device is a cap or helmet-shaped to fit onto a head of an individual to be treated. Preferably, the device is helmet-shaped to fit onto the head of an individual to be treated. Alternatively, the device is cap-shaped to fit onto the head of an individual to be treated. In one embodiment, the device may include free electrodes that may be placed onto a CNS/CSF-system. In one embodiment, the free electrodes may be attachable onto the device. In one embodiment, the free electrodes may be repositionable in respect of the device, and/or may be removable and re-attachable onto the device.

According to one aspect, the invention includes a device for inducing a controlled fluid transport in a central nervous system (CNS) and/or in a cerebrospinal fluid (CSF) system by electro-osmosis, the device comprising a mechanically connected body, at least two electrodes arranged spaced apart on said mechanically connected body, and electric wiring, wherein the mechanically connected body and the electrodes are configured to be placed onto the CNS/CSF-system to establish electrical communication between the electrodes and the CNS/CSF-system in accordance with method step b), and the wiring is configured to allow control of the electrodes by a control unit in accordance with method step c).

According to one embodiment, the device comprises at least three electrodes arranged spaced apart on said mechanically connected body, of which at least two are intended to act as anodes, and at least one is intended to act as cathode. According to one embodiment, the device comprises at least four electrodes arranged spaced apart on said mechanically connected body, of which at least three are intended to act as anodes, and at least one is intended to act as cathode. Preferably, the device comprises at least five electrodes, of which at least four are intended to act as anodes, and at least one is intended to act as cathode. Preferably, the device comprises at least eight electrodes, of which at least seven are intended to act as anodes, and at least one is intended to act as cathode. Preferably, the device comprises at least eleven electrodes, of which at least ten are intended to act as anodes, and at least one is intended to act as cathode. Preferably, the device comprises at least fourteen electrodes, of which at least thirteen are intended to act as anodes, and at least one is intended to act as cathode.

According to one embodiment, the device comprises at least one set of electrodes arranged in a row along the mechanically connected body. In one embodiment, the device comprises a second set of electrodes arranged in a second row along the mechanically connected body. Preferably, the set of electrodes arranged in a row is intended to act as anodes. According to one embodiment, the device comprises a set of electrodes arranged along a circumference of the mechanically connected body. Hence, the device may apply an electric field from all directions along its circumference towards the CNS/CSF-system. This allows a better and more fine-tuned control of the induced fluid flow inside the CNS/CSF-system.

According to one embodiment, at least one electrode is arranged to be placed on top of an individual's head. Preferably, the electrode placed on top of the head is a cathode, and generates a fluid flow towards superior sagittal sinus. In one embodiment, the device comprises at least one additional cathode positioned to allow drawing a fluid flow towards a lateral ventricle. Preferably, the device is configured so that, when the device is placed onto an individual, the electrodes are placed in electric communication with the CNS/CSF-system of the individuals, preferably on an individual's head. Preferably, the device comprises at least one electrode intended to function as a cathode and which cathode is arranged to be positioned on the crown of an individual's head when the device is in use. In one embodiment at least one electrode is placed on the dura mater of an individual. This could be the case if the individual suffers severe skull damage. In a preferred treatment, the device is configured so that, when the device is placed onto an individual's head, at least some electrodes are placed in electrical communication with the individual's skull. In one embodiment, the device is configured so that, when the device is placed onto an individual, said electrodes are placed in electrical communication with an individual's skin.

According to one embodiment, the mechanically connected body is a net, a cap or a helmet configured to fit onto the head of an individual to be treated, and to establish electrical communication between the electrodes of the device and the CNS/CSF-system of the individual at predetermined positions.

Preferably, the device comprises wiring configured to electrically connect said electrodes to one or more electric potential and/or electric current generators. The wiring may comprise an electrical network, and electric contacts allowing connection with the one or more electric potential and/or electric current generators. According to one embodiment the wiring is configured to admit independent control of the electric potential and/or electric current applied to at least two sets of electrodes in said device. Preferably, at least one set comprise one or more electrode(s) each configured to act as cathodes, and at least one set comprise one or more electrode(s) each configured to act as anodes. Preferably the wiring is configured so that each set of anodes is individually controllable relative to the other set. According to one embodiment, the device is configured to admit independent control of the electric potential and/or electric current applied to each individual electrode. Preferably, the wiring is configured to allow individual control of each set of electrodes.

According to one aspect, the invention comprises a computer program module configured to induce a computer to perform any method steps described herein, e.g. method steps a1) to a3).

According to one aspect, the invention comprises a computer program module configured to induce a computer or a system to perform any method steps described herein, e.g. method steps a1) to a3), a) and c).

According to one embodiment, the computer program module is configured to induce a computer to perform one or more additional method steps as appended in the claims.

A computer program module may comprise a subroutine of a computer program, a computer program, a computer or microcontroller programmed with a computer program, or a computer program product, such as computer program memory having a computer program stored therein.

According to one aspect, the invention includes a system for inducing a controlled fluid transport in a central nervous system (CNS) and/or in cerebrospinal fluid (CSF) system by electro-osmosis, comprising:
  a device comprising at least two electrodes adapted to be placed in electrical communication with the central nervous system (CNS) and/or cerebrospinal fluid (CSF) system,
  a control unit configured to control an application of electric potentials and/or electric currents to said electrodes in said device, and
  a computer program module configured to receive information as indicated in method step a) in claim 1 and to control the control unit to perform method step c).

According to one embodiment, the system comprises a computer program module configured to perform method steps a1) to a3).

According to one embodiment, the system comprises a device according to any of the device claims in the appended claims.

According to one embodiment, the system comprises a control unit comprising one or more electric potential and/or electric current generators configured to supply electric potentials and/or electric currents to the electrodes of said device in accordance with the method of claim 1.

The invention is not limited to the detailed description, the examples, and the drawings, but may be varied freely within the framework of the following claims. In particular, features disclosed relative to the inventive method may be freely adapted for use in the device, in the system or in the computer program model, as applicable, and vice versa.

Figure 8:
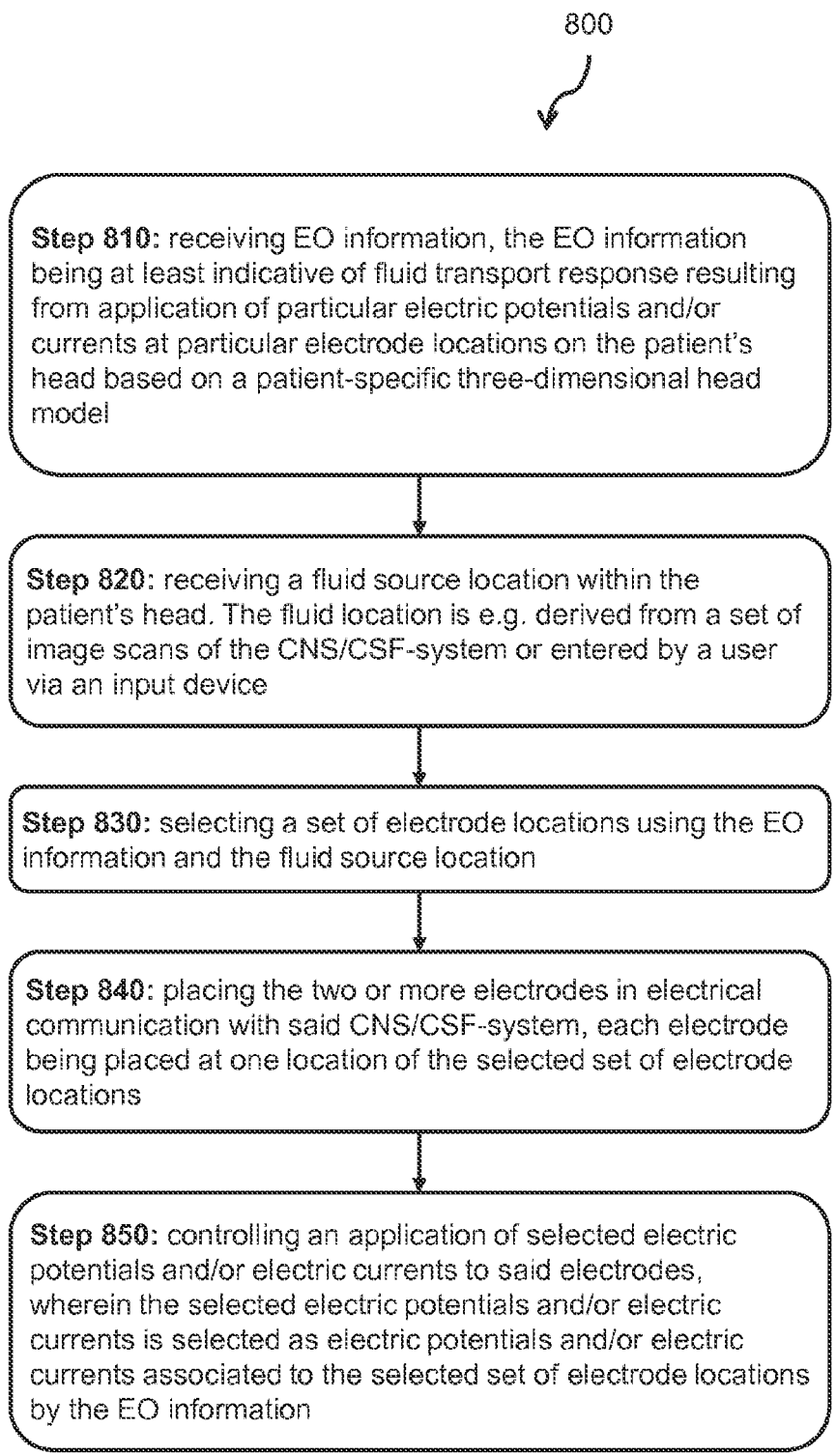
FIG. 8 shows the flowchart of the method in the treatment of patient.

FIG. 8 shows a flowchart of a method 800 according to one or more embodiments of the present disclosure. The method is for inducing a controlled fluid transport in a central nervous system, CNS, and/or in a cerebrospinal fluid, CSF, system of a patient by electro-osmosis, EO, via two or more electrodes placed at selected locations on the patients head, the method comprises:
  Step 810: receiving EO information, the EO information being at least indicative of fluid transport response resulting from application of particular electric potentials and/or currents at particular electrode locations on the patient's head based on a patient-specific three-dimensional head model.

In one embodiment, the EO information comprises information on electrode locations and/or on electrode potentials and/or electrode currents selected to achieve a controlled fluid transport or fluid transport response in said CNS/CSF-system.

In one embodiment, the EO information is received by generating the EO information by a computer simulation of induced fluid transport in the patient-specific three-dimensional head model of said CNS/CSF-system.

The patient-specific three-dimensional head model is typically generated based on a set of image scans of the CNS/CSF-system. The simulation is typically performed by simulating the fluid transport response from applying electric potentials and/or currents via at least one simulated anode electrode and at least one simulated cathode electrode placed in electrical communication with said CNS/CSF-system of said patient-specific three-dimensional head model.

In other words, a simulation is performed assuming that electrodes placed at a selected set of electrode locations where associated and particular electric potentials and/or currents are applied at particular electrode locations on the patient's head using the patient-specific three-dimensional head model. From evaluating the patient-specific three-dimensional head model with the particular electric potentials and/or currents, a fluid transport response can then be obtained. This is typically indicative of flow of fluid from a fluid source location to a fluid target location, such as from an edema to the superior sagittal sinus.

In one embodiment, the EO information is received by retrieving predetermined EO information from a memory, e.g. retrieved from an established database/look-up table and/or from historical simulations.

In one embodiment, the EO information is received by receiving user input from an input device, e.g. a clinician entering selected locations for electrodes and/or electric potentials and/or electric currents based on previous experience of patient treatment.

Step 820: receiving a fluid source location within the patient's head. The fluid location is e.g. derived from a set of image scans of the CNS/CSF-system or entered by a user via an input device.

Step 830: selecting a set of electrode locations using the EO information and the fluid source location. The electrode locations may be selected as locations providing a desired or optimal fluid transport response for a set of electrode locations given by the EO information.

In one embodiment, the step of selecting a set of electrode locations further comprises designating each location as a cathode or anode location where a particular electric potential and/or current should be applied.

Step 840: placing the two or more electrodes in electrical communication with said CNS/CSF-system, each electrode being placed at one location of the selected set of electrode locations.

In other words, two or more electrodes are attached to the patient's head at the selected set of electrode locations. If the helmet-like device provided with a plurality of electrodes having predetermined electrode locations, a set or sub-set of the plurality of electrodes may be activated, as further illustrated in relation to FIG. 2A-D.

Step 850: controlling an application of selected electric potentials and/or electric currents to said electrodes, wherein the selected electric potentials and/or electric currents is selected as electric potentials and/or electric currents associated with the selected set of electrode locations by the EO information. This way, a controlled fluid transport in said CNS/CSF-system can be introduced.

In one embodiment, the method further comprises selecting a region of the CNS/CSF-system that is to be drained of fluid and receiving a fluid target location as the location of the selected region of the CNS/CSF-system that is to receive fluid. Further, the step of placing electrodes comprises b1) placing at least one cathode electrode in electrical communication with the CNS/CSF-system in a position behind the region that is to receive fluid, e.g. as viewed from the region that is to be drained of fluid, and b2) placing at least one anode electrode in electrical communication with the CNS/CSF-system in spaced-apart positions behind the region that is to be drained of fluid, as viewed from the region that is to receive fluid, e.g. the superior sagittal sinus.

In one embodiment, the step of controlling 850 further comprises c1) controlling, e.g. with a control unit, the application of electric potential and/or electric current to at least one cathode electrode and to at least one anode electrode so as to focus a fluid transport from a region selected to be drained of fluid towards a region selected to receive fluid.

In one example, a fluid transport is focused from the region to a fluid target location.

In one embodiment, the said set of image scans, is a set of CT-image scans and/or a set of multimodal medical image scans, such as Magnetic Resonance Imaging, MRI, image scans and/or ultrasound image scans and/or Positron Emission Tomography, PET, image scans. It is understood that further suitable or available methods of obtaining image scans may be used without deviating from the present disclosure.

In one embodiment, the patient-specific three-dimensional head model of said CNS/CSF-system is generated using the set of image scans. In this embodiment, the method further comprises a1) receiving in a computer memory at least one set of image scans of the CNS/CSF-system, a2) generating the patient-specific three-dimensional head model of said CNS/CSF-system based on the received set of image scans, e.g. by smoothed-voxel approach, and a3) simulating, with a computer, a fluid transport in the patient-specific three-dimensional head model in response to applying electric potentials and/or currents via at least one simulated anode electrode and at least one simulated cathode electrode placed at selected locations and in electrical communication with said CNS/CSF-system to generate the EO information.

In one example, the patient-specific three-dimensional head model is developed using a smoothed-voxel approach based on image scans of a patient. First, image scans of the patient are segmented to voxels representing the CSN/CSF-system, e.g. using Expectation-Maximization (EM) algorithm (Dempster et al., 1977). The voxels are then converted to meshes using various smoothing algorithms (e.g. an algorithm developed by Boyd and Müller (2006)), together with material properties assigned to different parts of the CSN/CSF-system, forming a patient-specific three-dimensional finite element head model.

The documents referred to are Dempster A P, Laird N M, Rubin D B, "Maximum likelihood from incomplete data via the EM algorithm", Journal of the Royal Statistical Society: Series B (Methodological). 1977 September; 39(1):1-22 and Boyd S K, Müller R. "Smooth surface meshing for automated finite element model generation from 3D image data", Journal of Biomechanics. 2006 Jan. 1; 39(7):1287-95.

In one embodiment, the selected set of electrode locations includes locations for at least three anode electrodes in a position behind the region to be drained as seen from the region to receive the fluid, e.g. the superior sagittal sinus.

In one embodiment, the selected set of electrode locations includes locations for at least two anode electrodes in a position behind the region to be drained as seen from the region to receive the fluid, e.g. the superior sagittal sinus.

In one embodiment, the selected set of electrode locations includes locations for at least one anode electrode in a position behind the region to be drained as seen from the region to receive the fluid.

In one embodiment, said CNS/CSF-system is afflicted with edema, and the method comprises selecting the fluid source location as a region comprising the edema and targeted to be drained of fluid, simulating a fluid transport in a direction away from the edema using said patient-specific three-dimensional head model, and controlling the fluid transport and the application of electric potentials and/or electric currents to said electrodes to control a fluid transport away from the edema.

In one embodiment, said CNS/CSF-system comprises a glymphatic flow, and the method comprises selecting the fluid source location as a region comprising the glymphatic flow and targeted to be drained of fluid or targeted as a region for modulating the fluid, simulating a modulation/modification of the glymphatic flow using said patient-specific three-dimensional head model, and controlling the fluid transport and the application of electric potentials and/or electric currents to said electrodes to control modulation of the glymphatic flow.

In one embodiment, said CNS/CSF-system includes a brain afflicted with edema, and the method includes controlling the fluid transport so as to drive at least one fluid away from the edema and towards a lateral brain ventricle and/or towards a superior sagittal sinus.

In one embodiment, said patient-specific three-dimensional head model includes a 3D-model of the CNS/CSF-system.

In one embodiment, said patient-specific three-dimensional head model includes information on a fiber structure within the CNS/CSF-system.

In one embodiment, said patient-specific three-dimensional head model comprises information on damaged nervous tissue and on healthy nervous tissue.

In one embodiment, said patient-specific three-dimensional head model includes a 3D-model of a brain and/or of cerebrospinal fluid and/or of scalp and/or of brain ventricles and/or of skull bone.

In one embodiment, the method further includes placing a helmet-like device comprising a mechanically connected body and at least four spaced-apart electrodes in electrical communication with the CNS/CSF-system to be treated. The electrodes are typically placed in electrical communication with the CNS/CSF-system when the patient is wearing the helmet-like device. In one example, three electrodes are designated as anode electrodes and one electrode is designated as a cathode electrode.

In one embodiment, the method further includes placing a device, e.g. a helmet-like device, comprising a mechanically connected body and at least two spaced-apart electrodes in electrical communication with the CNS/CSF-system to be treated. The electrodes are typically placed in electrical communication with the CNS/CSF-system when the patient is wearing the helmet-like device. The device may e.g. be a net, a cap or a helmet configured to fit onto the head of an individual to be treated, thereby placing electrodes in electrical communication with the CNS/CSF-system to be treated at predetermined positions/locations on the patient's head.

Figure 9:
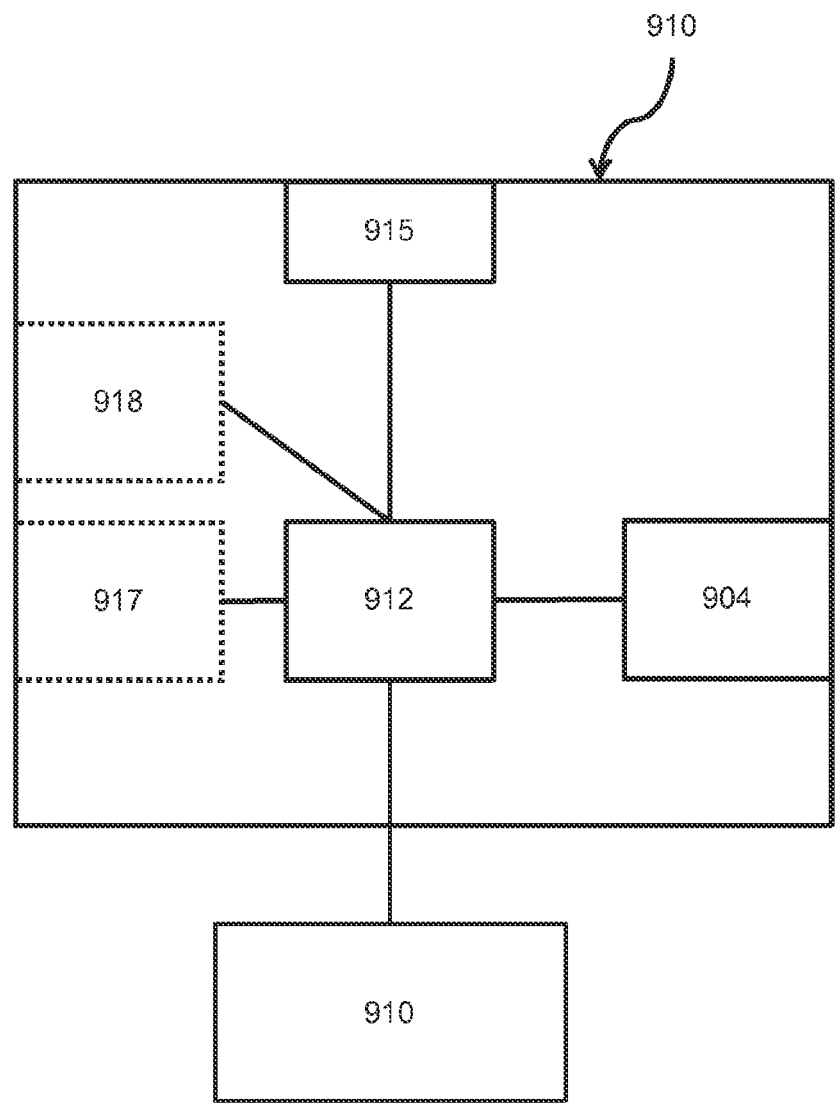
FIG. 9 shows the components and working process of a control unit.

FIG. 9 shows the control unit 910 according to one or more embodiments of the present disclosure. The control unit 910 may be in the form of e.g. an Electronic Control Unit, a server, an on-board computer, a stationary computing device, a laptop computer, a tablet computer, a handheld computer, a wrist-worn computer, a smartwatch, a smartphone or a smart TV. The control unit 910 may comprise processing circuitry 912 communicatively coupled to a transceiver 904 configured for wired or wireless communication. The control unit 910 may further comprise at least one optional antenna (not shown in the figure). The antenna may be coupled to the transceiver 904 and is configured to transmit and/or emit and/or receive wired or wireless signals in a communication network, such as WFi, Bluetooth, 3G, 4G, 5G etc. In one example, the processing circuitry 912 may be any of a selection of processing circuitry and/or a central processing unit and/or processor modules and/or multiple processors configured to cooperate with each other. Further, the control unit 910 may further comprise a memory 915. The memory 915 may e.g. comprise a selection of a hard RAM, disk drive, a floppy disk drive, a flash drive or other removable or fixed media drive or any other suitable memory known in the art. The memory 915 may contain instructions executable by the processing circuitry to perform any of the steps or methods described herein. The processing circuitry 912 may optionally be communicatively coupled to a selection of any of the transceiver 904, the memory 915 and/or any electrodes. The control unit 910 may be configured to send/receive control signals directly to any of the above-mentioned units or to external nodes or to send/receive control signals via the wired and/or wireless communications network.

The wired/wireless transceiver 904 and/or a wired/wireless communications network adapter may be configured to send and/or receive data values or parameters as a signal to or from the processing circuitry 912 to or from other external nodes.

In an embodiment, the transceiver 904 communicates directly to external nodes or via the wireless communications network.

In one or more embodiments the control unit 910 may further comprise an input device 917, configured to receive input or indications from a user and send a user input signal indicative of the user input or indications to the processing circuitry 912.

In one or more embodiments the control unit 910 may further comprise a display 918 configured to receive a display signal indicative of rendered objects, such as text or graphical user input objects, from the processing circuitry 912 and to display the received signal as objects, such as text or graphical user input objects.

In one embodiment the display 918 is integrated with the user input device 917 and is configured to receive a display signal indicative of rendered objects, such as text or graphical user input objects, from the processing circuitry 912 and to display the received signal as objects, such as text or graphical user input objects, and/or configured to receive input or indications from a user and send a user-input signal indicative of the user input or indications to the processing circuitry 912.

In a further embodiment, the control unit 910 may further comprise and/or be coupled to one or more additional sensors (not shown in the figure) configured to receive and/or obtain and/or measure physical properties pertaining to the location and/or patient and/or device E.g. a temperature sensor measuring ambient air temperature.

In one or more embodiments, the processing circuitry 912 is further communicatively coupled to the input device 917 and/or the display 918 and/or the additional sensors and/or any of the units described herein.

In embodiments, the communications network communicate using wired or wireless communication techniques that may include at least one of a Local Area Network (LAN), Metropolitan Area Network (MAN), Global System for Mobile Network (GSM), Enhanced Data GSM Environment (EDGE), Universal Mobile Telecommunications System, Long term evolution, High Speed Downlink Packet Access (HSDPA), Wideband Code Division Multiple Access (W-CDMA), Code Division Multiple Access (CDMA), Time Division Multiple Access (TDMA), Bluetooth®, Zigbee®, Voice over Internet Protocol (VoIP), LTE Advanced, IEEE802.16m, WirelessMAN-Advanced, Evolved High-Speed Packet Access (HSPA+), 3GPP Long Term Evolution (LTE), Mobile WiMAX (IEEE 802.16e), Ultra Mobile Broadband (UMB) (formerly Evolution-Data Optimized (EV-DO) Rev. C), Fast Low-latency Access with Seamless Handoff Orthogonal Frequency Division Multiplexing (Flash-OFDM), High Capacity Spatial Division Multiple Access (iBurst®) and Mobile Broadband Wireless Access (MBWA) (IEEE 802.20) systems, High Performance Radio Metropolitan Area Network (HIPERMAN), Beam-Division Multiple Access (BDMA), World Interoperability for Microwave Access (Wi-MAX) and ultrasonic communication, etc., but is not limited thereto.

Moreover, it is realized by the skilled person that the control unit 910 may comprise the necessary communication capabilities in the form of e.g. functions, means, units, elements, etc., for performing the present solution. Examples of other such means, units, elements and functions are: processors, memory, buffers, control logic, encoders, decoders, rate matchers, de-rate matchers, mapping units, multipliers, decision units, selecting units, switches, interleavers, de-interleavers, modulators, demodulators, inputs, outputs, antennas, amplifiers, receiver units, transmitter units, DSPs, MSDs, TCM encoder, TCM decoder, power supply units, power feeders, communication interfaces, communication protocols, etc. which are suitably arranged together for performing the present solution.

Especially, the processing circuitry and/or processing means of the present disclosure may comprise one or more instances of processing circuitry, processor modules and multiple processors configured to cooperate with each-other, Central Processing Unit (CPU), a processing unit, a processing circuit, a processor, an Application Specific Integrated Circuit (ASIC), a microprocessor, a Field-Programmable Gate Array (FPGA) or other processing logic that may interpret and execute instructions. The expression "processing circuitry" and/or "processing means" may thus represent a processing circuitry comprising a plurality of processing circuits, such as, e.g., any, some or all of the ones mentioned above. The processing means may further perform data processing functions for inputting, outputting, and processing of data comprising data buffering and device control functions, such as user interface control, or the like.

Finally, it should be understood that the invention is not limited to the embodiments described above, but also relates to and incorporates all embodiments within the scope of the appended independent claims.

Enumerated Embodiments

Embodiment 1. A method for inducing a controlled fluid transport in a central nervous system (CNS) and/or in a cerebrospinal fluid (CSF) system by electro-osmosis, comprising:
a) receiving information on electrode location and/or on electrode potential and/or electrode current selected to achieve a controlled fluid transport in said CNS/CSF-system, wherein the information is generated by a computer simulation of induced fluid transport in a computer model of said CNS/CSF-system, the computer model being generated based on a set of image scans of the CNS/CSF-system and the simulation being performed by simulating the fluid transport response from applying electric potentials and/or currents via at least one simulated anodes and at least one simulated cathode placed in electrical communication with said CNS/CSF-system in said computer model,
b) placing at least two electrodes in electrical communication with said CNS/CSF-system, and
c) controlling with a control unit an application of electric potentials and/or electric currents to said electrodes based on the received information from the computer simulation, to induce a controlled fluid transport in said CNS/CSF-system.

Embodiment 2. A method according to claim 1, characterized in that the method comprises selecting a region of the CNS/CSF-system that is to be drained of fluid, and selecting a region of the CNS/CSF-system that is to receive fluid, and that method step b) comprises:
b1) placing at least one cathode in electrical communication with the CNS/CSF-system in a position behind the region that is to receive fluid, as viewed from the region that is to be drained of fluid, and
b2) placing at least one anodes in electrical communication with the CNS/CSF-system in spaced-apart positions behind the region that is to be drained of fluid, as viewed from the region that is to receive fluid.

Embodiment 3. A method according to claim 1 or 2, characterized in that method step c) comprises:
c1) controlling with a control unit the application of electric potential and/or electric current to at least one cathode and to at least one anode so as to focus a fluid transport from a region selected to be drained of fluid towards a region selected to receive fluid.

Embodiment 4. A method according to claim 1, characterized in that said set of image scans, is a set of CT-image scans.

Embodiment 5. A method according to claim 1, characterized in that the method further comprises:
a1) receiving in a computer memory at least one set of image scans of the CNS/CSF-system,
a2) generating a computer model of said CNS/CSF-system based on the received set of image scans, and
a3) simulating with a computer a fluid transport in the computer model of said CNS/CSF-system in response to applying electric potentials and/or currents via at least one simulated anode and at least one simulated cathode placed in electrical communication with said CNS/CSF-system.

Embodiment 6. A method according to claim 5, characterized in that the method includes placing at least three anodes in a position behind the region to be drained as seen from the region to receive the fluid.

Embodiment 7. A method according to any of the preceding claims, characterized in that said CNS/CSF-system is afflicted with edema, and the method comprises
selecting the edema as a region to be drained of fluid,
simulating a fluid transport in a direction away from the edema, and
controlling the fluid transport and the application of electric potentials and/or electric currents to said electrodes to control a fluid transport away from the edema.

Embodiment 8. A method according to claim 7, characterized in that said CNS/CSF-system includes a brain afflicted with edema, and the method includes controlling the fluid transport so as to drive at least one fluid away from the edema and towards a lateral brain ventricle and/or towards a superior sagittal sinus.

Embodiment 9. A method according to any of the preceding claims, characterized in that said computer model includes a 3D-model of the CNS/CSF-system.

Embodiment 10. A method according to any of the preceding claims, characterized in that said computer model of the CNS/CSF-system includes information on a fiber structure within the CNS/CSF-system.

Embodiment 11. A method according to any of the preceding claims, characterized in that said computer model comprises information on damaged nervous tissue and on healthy nervous tissue.

Embodiment 12. A method according to any of the preceding claims, characterized in that said computer model includes a 3D-model of a brain, of cerebral fluid, of brain ventricles, of skull bone and of scalp.

Embodiment 13. A method according to any of the preceding claims, characterized in that method, includes placing a device comprising a mechanically connected body and at least four spaced-apart electrodes in electrical communication with the CNS/CSF-system to be treated.

Embodiment 14. A method according to claim 13, characterized in that the device is a net, cap or helmet configured to fit onto the head of an individual to be treated.

Embodiment 15. A device for inducing a controlled fluid transport in a central nervous system (CNS) and/or in a cerebrospinal fluid (CSF) system by electro-osmosis, the device comprising a mechanically connected body, at least two electrodes arranged spaced apart on said mechanically connected body, and electric wiring, wherein the mechanically connected body and the electrodes are configured to be placed onto the CNS/CSF-system to establish electrical communication between the electrodes and the CNS/CSF-system in accordance with method step b) of claim 1, and the wiring is configured to allow control of the electrodes by a control unit in accordance with method step c) of claim 1.

Embodiment 16. A device according to embodiment 15, characterized in that the device comprises at least three and/or four and/or five electrodes arranged spaced apart on said mechanically connected body.

Embodiment 17. A device according to any preceding embodiment, characterized in that the device comprises at least one set of electrodes arranged in a row along the mechanically connected body.

Embodiment 18. A device according to any preceding embodiment, characterized in that the device comprises a set of electrodes arranged along a circumference of the mechanically connected body.

Embodiment 19. A device according to any preceding embodiment, characterized in that the mechanically connected body is a net, a cap or a helmet configured to fit onto the head of an individual to be treated, and to establish electrical communication between the electrodes of the device and the CNS/CSF-system of the individual.

Embodiment 20. A device according to any preceding embodiment, characterized in that at least one electrode is arranged to be placed on top of the individuals head.

Embodiment 21. A device according to any preceding embodiment, characterized in that the wiring is configured to admit independent control of the electric potential and/or electric current applied to at least two sets of electrodes(s) in said device.

Embodiment 22. A device according to any preceding embodiment, characterized in that the device is configured to admit independent control of the electric potential and/or electric current applied to each individual electrode.

Embodiment 23. A computer program module characterized in that the computer program module is configured to induce a computer to perform the method step c) of claim 1.

Embodiment 24. A computer program module according to any preceding embodiment, characterized in that the computer program module is configured to induce a computer to perform method steps a1) to a4) of claim 5.

Embodiment 25. A computer program module characterized in that the computer program is configured to induce a computer to perform any method step of the methods described herein.

Embodiment 26. A system for inducing a controlled fluid transport in a central nervous system (CNS) and/or in a cerebrospinal fluid (CSF) system by electro-osmosis, comprising:

a device comprising at least two electrodes adapted to be placed in electrical communication with the central nervous system (CNS) and/or cerebrospinal fluid (CSF) system, a control unit configured to control an application of electric potentials and/or electric currents to said electrodes in said device, and a computer program module configured to perform any of the method steps described herein.

Embodiment 27. A system according to Embodiment 26, characterized in that the system further comprises:

a computer program module configured to perform any method steps described herein, in particular steps a1) to a3).

Embodiment 28. A system according to any of the preceding embodiments, characterized in that the device is a helmet-like device.

Embodiment 29. A system according to any of the preceding embodiments, characterized in that the control unit comprises one or more electric potential and/or electric current generators configured to supply electric potentials and/or electric currents to the electrodes of said device in accordance with the methods described herein.

The invention claimed is:

1. A method for inducing a controlled fluid transport in a central nervous system, CNS, and/or in a cerebrospinal fluid, CSF, system of a patient by electro osmosis, EO, between two or more electrodes placed at selected locations on the patient's head, comprising:

receiving EO information, the EO information being at least indicative of fluid transport response resulting from application of particular electric potentials and/or currents at particular electrode locations on the patient's head based on a patient-specific three-dimensional head model, receiving a fluid source location within the patient's head, selecting a set of electrode locations using the EO information and the fluid source location, placing the two or more electrodes in electrical communication with said CNS/CSF-system, each electrode being placed at one location of the selected set of electrode locations, and controlling an application of selected electric potentials and/or electric currents to said electrodes, wherein the selected electric potentials and/or electric currents is selected as electric potentials and/or electric currents associated to the selected set of electrode locations by the EO information, so as to induce a controlled fluid transport in said CNS/CSF-system.

2. The method according to claim 1, wherein the EO information comprises information on electrode location and/or on electrode potential and/or electrode current selected to achieve a controlled fluid transport in said CNS/CSF-system.

3. The method according to claim 1, wherein the EO information is received by generating the EO information by a computer simulation of induced fluid transport in the patient-specific three-dimensional head model of said CNS/CSF-system, wherein the patient-specific three-dimensional head model is generated based on a set of image scans of the CNS/CSF-system, and wherein the simulation is performed by simulating the fluid transport response from applying electric potentials and/or currents via at least one simulated anode electrode and at least one simulated cathode electrode placed in electrical communication with said CNS/CSF-system in said patient-specific three-dimensional head model.

4. The method according to claim 1, wherein the EO information is received by retrieving predetermined EO information from a memory.

5. The method according to claim 1, wherein the EO information is received by receiving user input from an input device.

6. The method according to claim 1, wherein the method further comprises:
selecting a region of the CNS/CSF-system that is to be drained of fluid, and receiving the fluid target location as the location of the selected region of the CNS/CSF-system that is to receive fluid, and
wherein placing electrodes further comprises:
b1) placing at least one cathode electrode in electrical communication with the CNS/CSF-system in a position behind the region that is to receive fluid, as viewed from the region that is to be drained of fluid, and
b2) placing at least one anode electrode in electrical communication with the CNS/CSF-system in spaced-apart positions behind the region that is to be drained of fluid, as viewed from the region that is to receive fluid.

7. The method according to claim 1, wherein controlling further comprises:
c1) controlling with a control unit the application of electric potential and/or electric current to at least one cathode electrode and to at least one anode electrode so as to focus a fluid transport from a region selected to be drained of fluid towards a region selected to receive fluid.

8. The method according to claim 1, wherein said set of image scans, is a set of CT-image scans and/or a set of multimodal medical image scans.

9. The method according to claim 1, wherein the method further comprises:
a1) receiving in a computer memory at least one set of image scans of the CNS/CSF-system,
a2) generating the patient-specific three-dimensional head model of said CNS/CSF-system based on the received set of image scans, and
a3) simulating, with a computer, a fluid transport in the patient-specific three-dimensional head model in response to applying electric potentials and/or currents via at least one simulated anode electrode and at least one simulated cathode electrode placed at selected locations and in electrical communication with said CNS/CSF-system to generate the EO information.

10. The method according to claim 9, wherein the selected set of electrode locations includes locations for at least three anode electrodes in a position behind the region to be drained as seen from the region to receive the fluid.

11. The method according to claim 9, wherein the selected set of electrode locations includes locations for at least one anode electrode in a position behind the region to be drained as seen from the region to receive the fluid.

12. The method according to claim 1, wherein
said CNS/CSF-system is afflicted with edema, and the method comprises selecting the fluid source location as a region comprising the edema and targeted to be drained of fluid,
simulating a fluid transport in a direction away from the edema using said patient-specific three-dimensional head model, and controlling the fluid transport and the application of electric potentials and/or electric currents to said electrodes to control a fluid transport away from the edema.

13. The method according to claim 1, wherein
said CNS/CSF-system is afflicted with glymphatic flow, and the method comprises selecting the fluid source location as a region comprising the glymphatic flow and targeted to be drained of fluid or targeted as a region for modulating the fluid, simulating a modulation/modification of the glymphatic flow using said patient-specific three-dimensional head model, and controlling the fluid transport and the application of electric potentials and/or electric currents to said electrodes to control modulation of the glymphatic flow.

14. The method according to claim 1, wherein said CNS/CSF-system includes a brain afflicted with edema, and the method includes controlling the fluid transport so as to drive at least one fluid away from the edema and towards a lateral brain ventricle and/or towards a superior sagittal sinus.

15. The method according to claim 1, wherein said patient-specific three-dimensional head model includes a 3D-model of the CNS/CSF-system.

16. The method according to claim 1, wherein said patient-specific three-dimensional head model includes information on a fiber structure within the CNS/CSF-system.

17. The method according to claim 1, wherein said patient-specific three-dimensional head model comprises information on damaged nervous tissue and on healthy nervous tissue.

18. The method according to claim 1, wherein said patient-specific three-dimensional head model includes a 3D-model of a brain and/or of cerebrospinal fluid and/or of scalp and/or of brain ventricles and/or of skull bone.

19. The method according to claim 1, wherein the method further includes: placing a helmet-like device comprising a mechanically connected body and at least four spaced-apart electrodes in electrical communication with the CNS/CSF-system to be treated.

20. The method according to claim 1, characterized in that method, includes placing a device comprising a mechanically connected body and at least two spaced-apart electrodes in electrical communication with the CNS/CSF-system to be treated.

21. A method according to claim 20, wherein the device is a net, cap or helmet configured to fit onto the head of an individual to be treated.

* * * * *